United States Patent [19]
Staar

[11] Patent Number: 5,165,131
[45] Date of Patent: Nov. 24, 1992

[54] TEETH CLEANING APPARATUS

[75] Inventor: Marcel J. H. Staar, Brussels, Belgium

[73] Assignee: Staar Development Co., S.A., Belgium

[21] Appl. No.: 633,534

[22] Filed: Dec. 28, 1990

[30] Foreign Application Priority Data

Dec. 29, 1989 [BE] Belgium .............. 08901389

[51] Int. Cl.[5] .................. A61C 17/22; A46B 13/02
[52] U.S. Cl. ................... 15/22.1; 128/62 A; 318/118
[58] Field of Search .............. 15/22.1, 22.2; 318/116, 318/118; 433/119; 128/62 A

[56] References Cited

U.S. PATENT DOCUMENTS

| | | | |
|---|---|---|---|
| 1,342,280 | 6/1920 | Fitzgerald | 15/22.1 |
| 2,319,205 | 5/1943 | Buck | 15/22.1 |
| 3,335,443 | 8/1967 | Parisi et al. | 15/22.1 |
| 3,375,820 | 4/1968 | Kuris et al. | 15/22.1 |
| 3,535,726 | 10/1970 | Sawyer | 15/22.1 |
| 3,828,770 | 8/1974 | Kuris et al. | 15/22.1 |
| 4,192,035 | 3/1980 | Kuris | 15/22.1 |
| 4,333,197 | 6/1982 | Kuris | 318/118 |
| 4,788,734 | 12/1988 | Bauer | 15/105 |
| 4,909,241 | 3/1990 | Burn | 15/22.1 |

FOREIGN PATENT DOCUMENTS

0324120 7/1989 European Pat. Off. .

Primary Examiner—Edward L. Roberts
Attorney, Agent, or Firm—Leydig, Voit & Mayer

[57] ABSTRACT

A teeth cleaning apparatus has a brush pivotally mounted in a brush holder. The brush has a teeth cleaning member such as bristles formed thereon. A vibrator exerts a vibratory force on the brush so that the teeth cleaning member moves back and forth in substantially its axial direction. The vibrator is driven by an electrical signal which preferably is of a frequency between 1,000 and 17,000 Hz and includes an audio frequency component of mixed frequency and amplitude representing music or other pleasant sounds which is transmitted to the auditory system of a person while brushing.

20 Claims, 4 Drawing Sheets

TEETH CLEANING APPARATUS

BACKGROUND OF THE INVENTION

This invention relates to a teeth cleaning apparatus that can reduce the monotony associated with cleaning the teeth and at the same time enhance the efficiency of manual cleaning.

Regular brushing of the teeth is extremely important for maintaining the health of the teeth and gums. However, many persons, and particularly children, are not willing to brush their teeth regularly because they find brushing the teeth with a conventional toothbrush to be a monotonous chore.

SUMMARY OF THE INVENTION

Accordingly, it is an object of the prsent invention to provide a teeth cleaning apparatus that is more pleasurable to use than a conventional toothbrush.

It is another object of the present invention to provide a teeth cleaning apparatus that can clean the teeth more efficiently than a conventional toothbrush.

It is still another object of the present invention to provide a teeth cleaning apparatus that can be operated by anyone familiar with the use of a conventional toothbrush.

A teeth cleaning apparatus according to the present invention has a brush comprising a brush handle and a teeth cleaning member, such as a bristle, secured to the handle. The brush handle is pivotally mounted on a brush holder. The brush holder supports a vibrator that vibrates the brush handle and causes the bristle or other teeth cleaning member to move substantially parallel to its axis. When the teeth cleaning member is placed against the teeth of a user of the apparatus, the vibration of the teeth cleaning member removes dirt, plaque, and other substances from the teeth.

The vibrator is preferably an electrical device that can be vibrated with a desired frequency by an alternating current electrical drive signal. The wave form of the drive signal can be constant over time, or it can be varied over time to vary the sensation imparted to the jaw of the user and make cleaning the teeth more pleasurable. The drive signal may also have an audio frequency corresponding to music, speech or other pleasant sounds.

DESCRIPTION OF THE PREFERRED EMBODIMENTS

Figure 1:
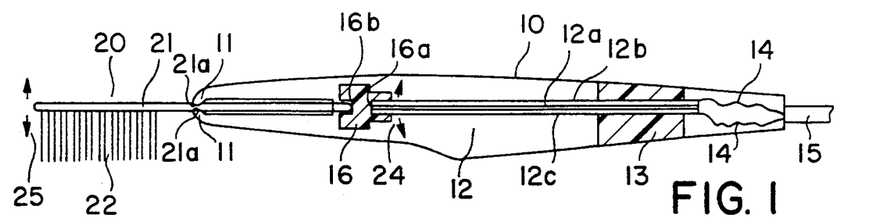
FIG. 1 is a schematic side cross-sectional view of an embodiment of a teeth cleaning apparatus according to the present invention.
Figure 2:
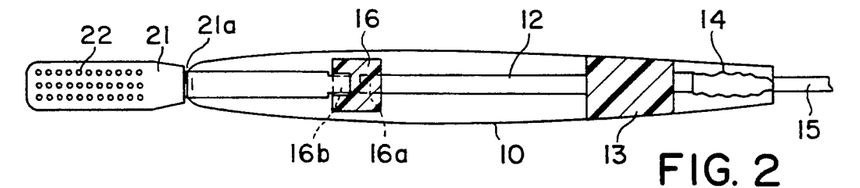
FIG. 2 is a schematic top cross-sectional view of the embodiment of FIG. 1.

A number of preferred embodiments of the present invention will now be described while referring to the accompanying drawings. FIGS. 1 and 2 schematically illustrate in cross section a first embodiment of a teeth cleaning apparatus according to the present invention as viewed from the side and from above, respectively. As shown in these figures, this embodiment has a hollow brush holder 10 that serves as a handle by which a user can grasp the cleaning apparatus. The brush holder 10 is preferably made of a material such as a molded plastic that is resistant to corrosion when exposed to water. A brush 20 is pivotally supported at one end of the brush holder 10. The brush 20 includes a handle 21 having an inner end disposed inside the brush holder 10 and an outer end that extends to the outside of the brush holder 10. One or more teeth cleaning members such as conventional toothbrush bristles 22 are secured to the outer end of the handle 21 and extend substantially perpendicularly from the handle 21. A pair of recesses 21a are formed in the top and bottom surfaces of the handle 21 between its inner and outer ends and are elastically held between elastically deformable jaws 11 of the brush holder 10. The engagement between the jaws 11 and the recesses 21a prevents the brush 20 from becoming detached from the brush holder 10 due to the forces exerted on the brush 20 during normal operation of the apparatus, but permits the brush 20 to be withdrawn from the brush holder 10 when an axial force is exerted on the handle 21 of the brush 20 by hand. At the same time, the engagement permits the handle 21 of the brush 20 to freely pivot in the jaws 11 of the brush holder 10 in the direction of arrows 25 in FIG. 1 so that the bristles 22 move substantially parallel to their axes.

Other means can be employed for pivotally connecting the brush 20 to the brush holder 10. For example, the brush 20 can be pivotally mounted on a pin secured to the end of the brush holder 10. Alternatively, instead of having recesses 21a, the handle 21 of the brush 20 can have projections or pins formed thereon that fit into recesses formed in the brush holder 10.

Vibratory motion is imparted to the brush handle 21 by a vibrator comprising an elongated plate-like piezoelectric element 12 mounted inside the brush holder 10. The piezoelectric element 12 has a piezoelectric crystal 12a with top and bottom surfaces on which electrodes 12b and 12c are formed. Piezoelectric elements suitable for use in the present invention are readily available as off-the-shelf components, and a conventional piezoelectric element can be employed. In many cases, the electrodes 12b and 12c are printed circuits formed on the surfaces of the piezoelectric crystal 12a. One end of the piezoelectric element 12 (the right end in FIG. 1) is supported by an electrically insulating support member 13, such as a piece of molded rubber secured to the inside of the brush holder 10, while the other end of the piezoelectric element 12 (the left end in FIG. 1) extends from the support member 13 as a cantilever. The left end of the piezoelectric element 12 is loosely coupled to the inner end of the brush handle 21 by a connector 16 that transmits up and down movement of the piezoelectric element 12 to the brush 20. In the present embodiment, the connector 16 is made of flexible rubber. It has a first cavity 16a that receives and is secured to the left end of the piezoelectric element 12 and a second cavity 16b that receives the inner end of the brush handle 21. If the connector 16 is sufficiently flexible to readily flex when the left end of the piezoelectric element 12 moves up and down, the dimensions of the second cavity 16b can be made slightly smaller than the dimensions of the inner end of the brush handle 21 so that when the inner end of the brush handle 21 is pressed into the second cavity 16b, the engagement between the inner surface of the second cavity 16b and the brush handle 21 will help to prevent the brush 20 from becoming disengaged from the brush holder 10.

Any other type of connection that can transmit the up and down movement of the left end of the piezoelectric element 12 to the inner end of the brush handle 21 can be employed, such as a pin that pivotally connects the piezoelectric element 12 to the inner end of the brush handle 21.

During operation of the apparatus, the electrodes 12b and 12c of the piezoelectric element 12 are connected to an unillustrated external AC power supply by lead wires 14 and a power supply cord 15 secured to the right end of the brush holder 10. When a voltage is applied to the electrodes 12b and 12c of the piezoelectric element 12, the piezoelectric element 12 will bend, the direction of bending being determined by the polarity of the voltage. In the present embodiment, the right end of the piezoelectric element 12 is restrained from movement by the support member 13, so when a voltage is applied to the electrodes 12b and 12c, the bending of the piezoelectric element 12 causes the free end (the left end) of the piezoelectric element 12 to move up or down as shown by arrows 24 in FIG. 1. When an alternating voltage is applied to the electrodes 12b and 12c, the free end of the piezoelectric element 12 moves up and down at a frequency equal to the frequency of the alternating voltage. The up and down movement of the piezoelectric element 12 is transmitted to the inner end of the brush handle 21, and the outer end of the brush handle 21 is moved up and down in the direction of arrows 25. As a result the bristles 22 are likewise moved up and down substantially parallel to their axes.

Figure 4:
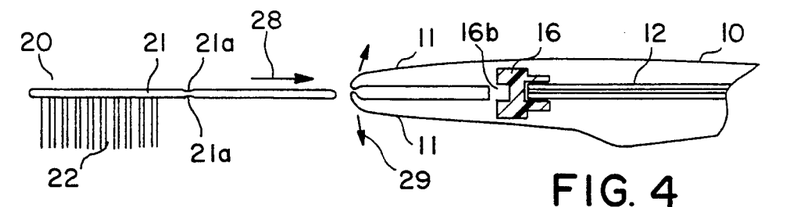
FIG. 4 is a schematic side cross-sectional view showing a brush being inserted into the brush holder of FIG. 1.

In this embodiment, the brush 20 is detachable from the brush holder 10 to enable the user to interchange or replace the brush 20. The user can remove the brush 20 from the brush holder 10 by grasping the brush 20 in his fingers and pulling in the axial direction of the brush 20. The bush 20 can be once again mounted in the brush holder 10 by inserting the brush handle 21 into the jaws 11 of the brush holder 10 and pressing axially on the brush 20 in the direction of arrow 28 in FIG. 4 until the inner end of the brush handle 21 engages with the second cavity 16b of the connector 16. The inner end of the brush handle 21 and the ends of the jaws 11 can be rounded to make it easier for the brush handle 21 to slide into the jaws 11. The thickness of the brush handle 21 is larger than the separation between the jaws 11 in an undeformed state so that when the handle 21 is inserted into the jaws 11, the jaws 11 are bent away from one another in the direction of arrows 29 in FIG. 4 and elastically grasp the upper and lower surfaces of the brush handle 21.

Figure 5:
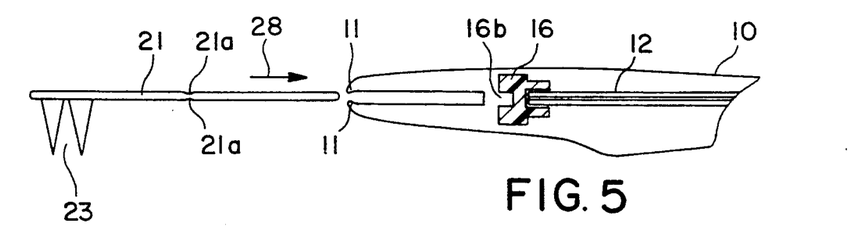
FIG. 5 is a schematic side cross-sectional view of a portion of the brush holder of FIG. 1 and a different type of brush that can be employed in the present invention.

The teeth cleaning members mounted on the brush 20 are not limited to bristles 22, and any member that can exerting a cleaning effect when placed into vibratory contact with the teeth can be employed. FIG. 5 illustrates an example of a removable brush 20 having teeth cleaning members in the form of conical rubber projections 23 secured to the outer end of the brush 20. Such rubber projections 23 are commonly found on the ends of conventional toothbrushes and are useful for massaging the gums and cleaning the gaps between the teeth. The brush 20 of FIG. 5 can be mounted in the brush holder 10 in the same manner as the brush 20 of FIG. 4.

A teeth cleaning apparatus according to the present invention can be used in a variety of operating modes. When no voltage is applied to the piezoelectric element 12, the apparatus can be operated in a manual mode in which the brush holder 10 serves as simply an elongation of the brush handle 21, and the user brushes his teeth in exactly the same method as he would use with a conventional toothbrush by manually moving the bristles 22 of the brush 20 with respect to this teeth. If a voltage is supplied to the piezoelectric element 12, the apparatus can be operated in a fully automatic mode in which the user simply holds the brush holder 10 with the bristles 22 resting against his teeth, and the vibration of the piezoelectric element 12 causes the bristles 22 to vibrate towards and away from his teeth, removing fine particles, scraping away tartar, and massaging the gums. The bristles 22 are very rigid in the direction of their axes and act on the teeth like a large number of tiny hammers that abrade away unwanted material and films on the surface of the teeth. The apparatus is most effective when operated in a semi-automatic mode in which the user manually moves the brush holder 10 to brush his teeth in the manner as when using a conventional toothbrush and at the same time electricity is supplied to the piezoelectric element 12 to move the bristles 22 back and forth towards the teeth. Since the direction of movement of the bristles 22 when the piezoelectric element 12 is energized is orthogonal to the direction of movement of the bristles 22 during manual brushing, the two movements are complementary.

Figure 3:
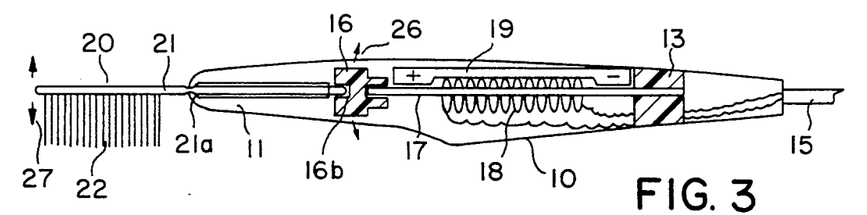
FIG. 3 is a schematic side cross-sectional view of another embodiment of the present invention.

FIG. 3 is a schematic side cross-sectional view of another embodiment of the present invention. This embodiment is similar to the embodiment of FIGS. 1 and 2 but employs a different type of electrically operated transducer element for vibrating the brush 20. The piezoelectric element 12 of FIG. 1 is replaced by a thin, flexible magnetic bar 17 having one end supported by a support member 13 secured to the inside of a brush holder 10 and a free end connected to the inner end of a brush handle 21 by a connector 16. The bar 17 can be made of any magnetic material, such as a ferro-magnetic substance. It can be magnetized with a desired polarity by an electrically conducting wire wrapped into a coil 18 around the bar 17. The ends of the coil 18 are connected to an unillustrated alternating current power supply by a power cord 20 secured to the end of the brush holder 10. A permanent magnet 19 is mounted inside the brush holder 10 opposing and separated from the bar 17. When a current is passed through the coil 18, the bar 17 is magnetized with a prescribed polarity and is attracted to or repulsed from the permanent magnet 19, depending on the polarity of the current. If an alternating current is passed through the coil 18, the free end of the bar 17 alternately bends towards and then away from the permanent magnet 19 with the frequency of the current as shown by arrows 26 in FIG. 3. The up and down movement of the free end of the bar 17 caused by the bending is transmitted to the inner end of the brush handle 21 by the connector 16, and the bristles 22 on the outer end of the brush 20 are moved up and down as shown by arrows 27. This embodiment can be used to clean the teeth in the same manner as the embodiment of FIG. 1. It can be used in a fully manual mode, in a fully automatic mode, or in a semi-automatic mode.

Figure 6A:
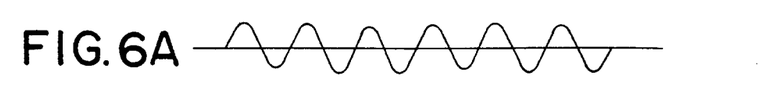
FIGS. 6A-6D are graphs of different examples of drive signals that can be employed in the present invention for vibrating the brush.
Figure 6B:
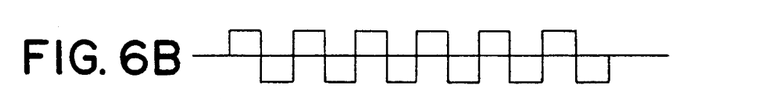

The wave form of the voltage applied to the vibrator of a teeth cleaning apparatus according to the present invention can vary. FIG. 6 illustrates various examples of wave forms that can be employed. As shown in FIGS. 6A and 6B, the voltage can be one having a constant frequency and amplitude. FIG. 6A shows a voltage having a sinusoidal wave form, while FIG. 6B shows a voltage having a square wave form. A square wave can be used when it is desired to alter the character of the vibration of the bristles 22 of the brush 20.

Figures 6C, 6D:
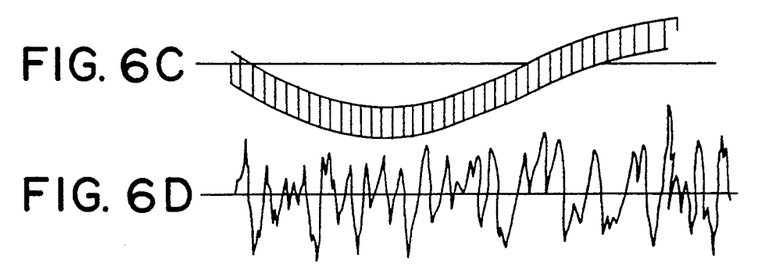

The tedium of brushing the teeth can be decreased by employing a wave form that varies the strength of the vibration over time. FIG. 6C illustrates a wave form comprising square waves of a first frequency modulated by an alternating wave form of a second, lower frequency. The strength of the vibration of the brush 20 will vary in accordance with the modulating frequency.

In a particularly preferred form of the present invention, the signal for exciting the vibrator is a signal at audio frequencies, such as the electrical signal generated by a radio, a tape recorder, or other audio reproduction device for driving a speaker or head phone. An example of such a signal is shown in FIG. 6D. The use of a signal at audio frequencies to drive the vibrator is particularly effective for reducing the tedium of brushing the teeth. The vibrations of the brush 20 at the audio frequency are imparted to the jaw of the user and from the jaw to the auditory system of the user, so the rhythm of the music driving the brush 20 can be extremely well perceived by the user.

Figure 7:
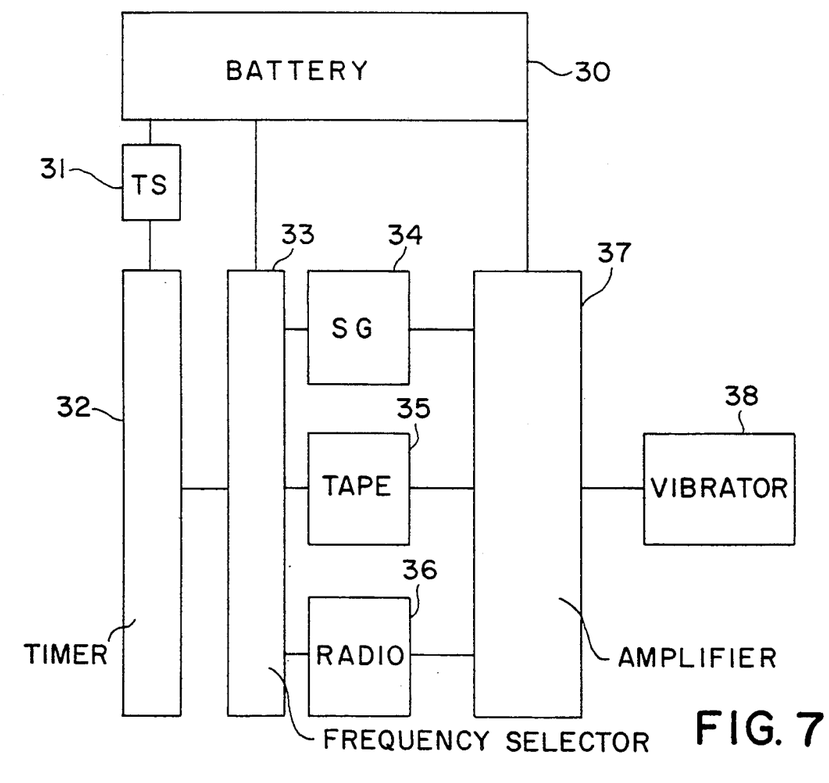
FIG. 7 is a block diagram of an example of a control system for the present invention.

FIG. 7 is a block diagram of a control circuit for use with a teeth cleaning apparatus of the present invention. The control circuit enables the user to select from a variety of frequencies for vibrating the brush 20. The control circuit is powered by a power supply such as a battery 30. A time selector 31 enables the user to set a timer 32 to the length of time for which the apparatus is to be operated. A frequency selector 33 enables the user to select one of a plurality of frequency sources for generating an alternating voltage of a desired frequency for driving the brush 20 of the cleaning apparatus. In this example, the frequency sources are a signal generator 34 for generating a signal having a predetermined wave form of a fixed frequency (such as one of those shown in FIGS. 6A–6C), a cassette tape player 35, and a radio 36. Alternatively, the frequency sources could include a record player, a compact disc player, or a semiconductor memory having music, speech or other pleasant sounds digitally stored therein. The output signal of the frequency source selected by the frequency selector 33 is provided to an amplifier 37, which amplifies the signal and applies it to the brush vibrator 38 of the teeth cleaning apparatus. If the cassette tape player 35 or the radio 36 is selected as the frequency source, the user can listen to music at the same time that he cleans his teeth. The output signals of the cassette tape player 35 and the radio 36 can be the same low-level signals used to drive a head phone or an external speaker, so elements 35 and 36 can be conventional off-the-shelf items.

The frequency of the signal for driving the vibrator is not restricted to any particular value, although the most effective frequencies of vibration of the bristles for cleaning purposes are thought to be in the range of around 1,000 to 17,000 Hz. Since some frequencies in music recordings may be below this range (i.e. 100 to 1000 Hz), it is also possible to use a signal comprising a desired high frequency (such as 12,000 Hz) modulated by the frequencies of a musical recording so as to obtain both a high cleaning effectiveness and a pleasant sensation from the musical frequencies.

If the exciting frequency is chosen so as to be near the resonant frequency of the moving assembly including the piezoelectric element, the brush 20 can be vibrated with great force using only a small exciting voltage.

Figure 8:
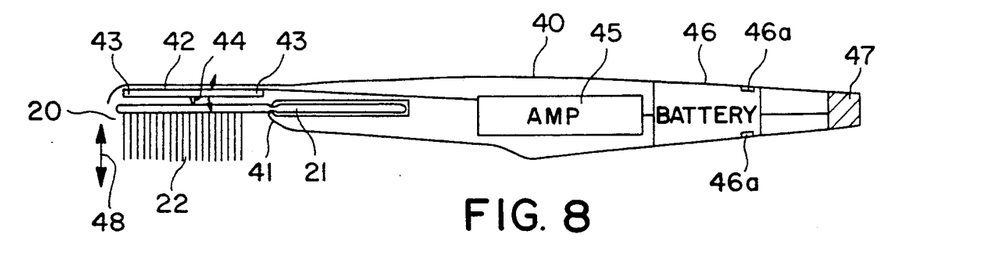
FIG. 8 is a schematic side cross-sectional view of another embodiment of the present invention in which a vibrating force is applied directly to the head of a brush.

FIG. 8 is a schematic side cross-sectional view of a preferred embodiment of the present invention. This embodiment includes a brush holder 40 having jaws 41 that pivotally support a removable brush 20 having an inner end loosely received inside the brush holder 40 and an outer end having teeth cleaning members in the form of bristles 22 secured thereto. The brush 20 is vibrated by a vibrator comprising a thin, plate-like piezoelectric element 42 supported by the brush holder 40 adjacent the head of the brush 20 above the bristles 22. Like the piezoelectric element of the embodiment of FIG. 1, the piezoelectric element 42 comprises a piezoelectric crystal 42a having electrodes 42b and 42c formed on its top and bottom surfaces. The ends of the piezoelectric element 42 are elastically supported by rubber rings 43 or similar members secured to the brush holder 40. A rigid contact member such as a conical stud 44 made of hard rubber or the like projects from the middle of the piezoelectric element 42 and engages the brush head.

Figure 9A:
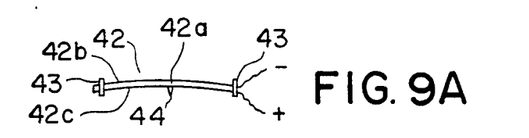
FIGS. 9A-9C illustrate the movement of the piezoelectric element of the embodiment of FIG. 8 when a voltage is applied thereto.
Figure 9B:
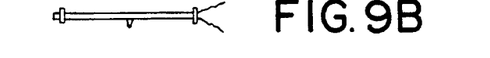
Figure 9C:
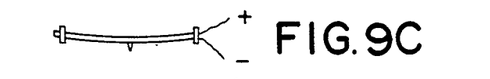

FIG. 9 illustrates the movement of the piezoelectric element 42 when a voltage is applied to its electrodes 42b and 42c. When a voltage of a first polarity is applied, the piezoelectric element 42 flexes upwards as shown by FIG. 9A, and when the polarity is reversed, the piezoelectric element 42 flexes downwards as shown by FIG. 9C. When no voltage is applied, the piezoelectric element 42 is substantially straight, as shown in FIG. 9B. If an alternating voltage is applied to the electrodes 42a and 42b, the piezoelectric element 42 flexes up and down with the frequency of the applied voltage. As the piezoelectric element 42 vibrates up and down, the stud 44 engages the head of the brush 20 and causes the brush 20 to vibrate up and down in the direction of arrows 48 of FIG. 8. As a result the bristles 22 are moved up and down substantially parallel to their axes. The movement of the bristles 22 against the teeth of a user exerts the same cleaning effect as described with respect to the preceding embodiments.

Figure 10:
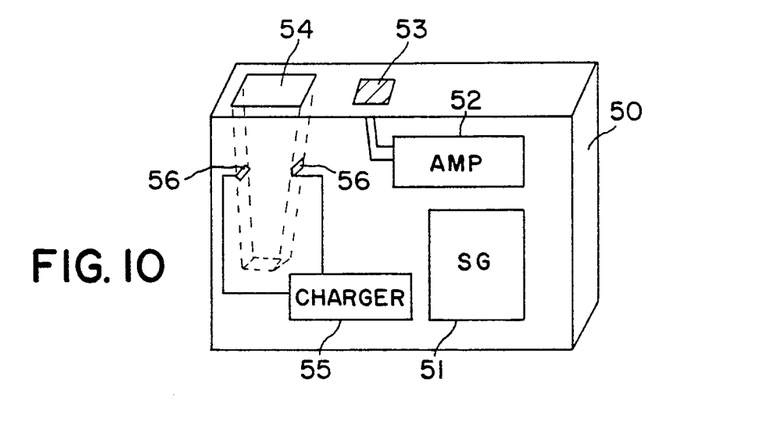
FIG. 10 is a block diagram of a storage unit for the embodiment of FIG. 8.

A signal for exciting the piezoelectric element 42 is generated by a signal generating system 51 inside a storage unit 50. The signal generating system 51 may comprise a simple signal generator, or it may include a timer, a frequency selector, and a musical reproduction device, like the control circuit illustrated in FIG. 7. The exciting signal is amplified by an amplifier 52 and transmitted to the teeth cleaning apparatus by a transmitter 53, such as a radio wave transmitter or an infrared transmitter. The transmitted signals are received by a radio wave or infrared receiver 47 mounted on the end of the brush holder 40 opposite the end that supports the brush 20. When the brush holder 40 is grasped by the hand of a user, the receiver 47 extends from the user's hand so that the transmitted signals can be easily received. The received signal is provided to an amplifier 45 mounted inside the brush holder 40, which amplifies the signal and supplies it to the electrodes of the piezoelectric element 42 as an exciting signal. The amplifier 45 and the receiver 47 are powered by a rechargeable battery 46 mounted inside the brush holder 40.

When not in use, the brush holder 40 is stored inside a cavity 54 formed in the storage unit 50. The storage unit 50 houses a battery charger 55 having electrical contacts 56 that project inwards from the inner surface of the cavity 54. When the brush holder 40 is placed into the cavity 54, the terminals 46a of the rechargeable battery 46 contact the electrical contacts 56 in the cavity 54, and the battery 46 is automatically recharged.

Since the vibrator of this embodiment is powered during use by a battery 46 inside the brush holder 40, a power cord between the storage unit 50 and the brush holder 40 is not necessary, making this embodiment particularly easy and safe to use.

Figure 11:
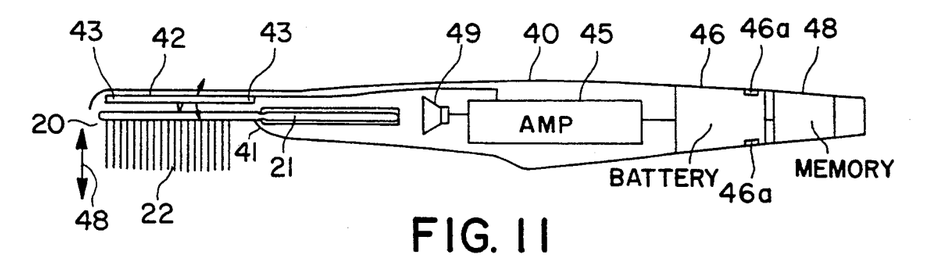
FIG. 11 is a schematic side cross-sectional view of an embodiment of the present invention having a signal generator disposed inside the brush holder.

If the brush 20 is to be vibrated at a single frequency, an oscillator circuit for generating an alternating current signal can be disposed inside the brush holder 40 of the teeth cleaning apparatus. As shown in FIG. 11, it is also possible to house a musical frequency generator 48 inside the brush holder 40 itself so as to make the teeth cleaning apparatus completely self-contained. The musical frequency generator 48 can comprise a semiconductor memory chip storing data corresponding to the sound desired to be produced. During the operation of the apparatus, the data from the memory chip can be converted to a signal and supplied to an amplifier 45 inside the brush holder 40, and the amplified signal can be applied to the electrodes of the piezoelectric element 42. The embodiment of FIG. 11 is otherwise identical in structure to the embodiment of FIG. 8.

In the preceding embodiments, a piezoelectric element is used to produce movement when a voltage is applied to the element. However, a piezoelectric element can also be used to generate a voltage when it is deformed by the application of an external force. When a teeth cleaning apparatus according to the present invention is being used in a semi-automatic mode, i.e., when the user is brushing his teeth manually at the same time that the brush vibrator is operating, a significant amount of energy is exerted by the hand of the user. If this energy is used to deform the piezoelectric element, the resulting electricity that is generated can be used to help power the piezoelectric element so as to generate the vibrations used to vibrate the brush. The voltage generated by the deformation of the piezoelectric element due to brushing has a much lower frequency (generally on the order of a few Hz) than the frequency of the exciting signal applied to the piezoelectric element to cause it to vibrate. Therefore, the voltage generated by the piezoelectric element due to manual brushing can be differentiated from the exciting frequency by means of diodes and filters. The generated voltage can then be applied to a battery as a charging voltage.

The piezoelectric element can be connected to the brush 20 so as to be deformed and generate a voltage in response to the up and down movement of the bristles 22 towards and away from the teeth of the user, i.e., movement of the brush 20 in the direction of arrows 24 in FIG. 1, preferably utilizing an arrangement such as that illustrated in FIG. 8.

Figure 12:
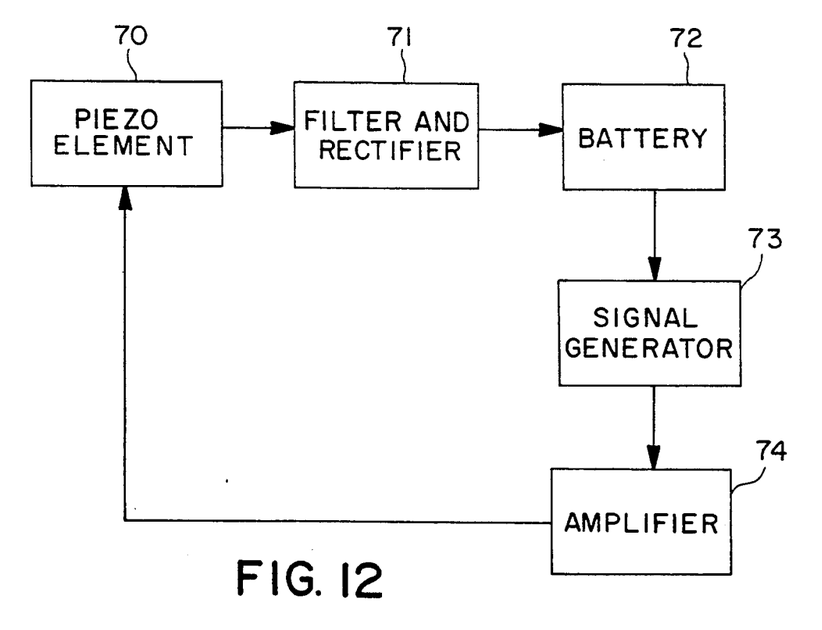
FIG. 12 is a block diagram of a control circuit for the embodiment of FIG. 11.

FIG. 12 is a block diagram of an example of a simple circuit for filtering and rectifying the generated voltage using a piezo-electric element as a generator at the same time it is vibrating in response to an impressed higher frequency voltage for causing the brush to vibrate for cleaning and/or for transmitting audio frequency signals to a user's auditory system. While the brush arrangement of FIG. 8 is preferred, an arrangement of brush holder and piezo-electric element as disclosed in the other figures may also be used, if desired.

The low-frequency voltage generated by the deformation of the piezoelectric element 42 (FIG. 8) is received from the electrodes of the element and filtered and rectified by a filter and rectifier circuit 71 (FIG. 12) and the rectified voltage is applied to a rechargeable battery 72. The battery 72 powers a signal generator 73 that generates an exciting signal for the piezoelectric element 70. The exciting signal is amplified by an amplifier 74. The amplified signal is applied to the electrodes of the piezoelectric element 70, and the piezoelectric element 70 is driven to oscillate in the same manner as in the embodiment of FIG. 1 or FIG. 8. The filter and rectifier circuit 71, the battery 72, the signal generator 73, and the amplifier 74 can be disposed either inside or outside of the brush holder 10.

In the preceding embodiments, the brush 20 is pivotally supported by the brush holder. However, any means of support can be employed that permits the up and down movement of the outer end of the brush 20 so that the brush cleaning members move substantially parallel to their axes. For example, in an embodiment employing a vibrator like the one used in FIG. 8, the inner end of the brush handle 21 could be elastically connected to the brush holder 10 by an elastic member.

What is claimed is:

1. A teeth cleaning apparatus comprising:
   a brush comprising an elongated brush handle and a teeth cleaning member carried by the handle and having an axis extending substantially perpendicular to the brush handle;
   a brush holder for supporting the brush handle to permit the movement of the brush handle in a prescribed direction such that the teeth cleaning member is moved substantially parallel to its axis; and
   a vibrator for vibrating the brush handle in the prescribed direction, the vibrator comprising a piezoelectric element having electrodes, a first end supported by the brush holder and restrained from movement, and a second end mechanically coupled to a brush handle.

2. A teeth cleaning apparatus comprising:
   a brush comprising an elongated brush handle having an end and a teeth cleaning member mounted on the end of the brush handle and having an axis extending substantially perpendicular to the brush handle;
   a brush holder for supporting the brush handle to permit the movement of the brush handle in a prescribed direction such that the teeth cleaning member is moved substantially parallel to its axis; and
   a vibrator for vibrating the brush handle in the prescribed direction, the vibrator comprising a piezoelectric element having electrodes, first and second ends supported by the brush holder, and a midportion having a contact member projecting therefrom, the end of the brush handle being disposed in the vicinity of the contact member of the piezoelectric element.

3. A teeth cleaning apparatus as claimed in claim 2 wherein the teeth cleaning member is a bristle.

4. A teeth cleaning apparatus as claimed in claim 2 wherein the vibrator comprises means for vibrating the brush handle in response to an electrical drive signal, further comprising a signal generator for generating the drive signal.

5. A teeth cleaning apparatus as claimed in claim 4 wherein the drive signal has a frequency in the range of 1,000–17,000 Hz.

6. A teeth cleaning apparatus as claimed in claim 4 wherein the vibrator comprises a piezoelectric element included in a movable assembly and the assembly has a resonant frequency of vibration, and the drive signal has a frequency close to the resonant frequency.

7. A teeth cleaning apparatus as claimed in claim 4 wherein the drive signal has a constant frequency.

8. A teeth cleaning apparatus as claimed in claim 2 further comprising means for generating electricity at one frequency from mechanical deformation of the element produced by a user while brushing and using the generated electricity to vibrate the element at a different frequency, and means for storage of the generated electricity.

9. A teeth cleaning apparatus comprising:
a brush comprising an elongated brush handle and a teeth cleaning member carried by the handle and having an axis extending substantially perpendicular to the brush handle;
a brush holder for supporting the brush handle to permit the movement of the brush handle in a prescribed direction such that the teeth cleaning member is moved substantially parallel to its axis;
a vibrator for vibrating the brush handle in the prescribed direction in response to an electrical drive signal; and
a signal generator for generating the drive signal, the drive signal comprising an audio signal of mixed amplitude and frequency.

10. A teeth cleaning apparatus as claimed in claim 9 wherein the vibrator comprises:
a magnetic bar having a first end supported by the brush holder and a second end capable of movement and coupled to the brush handle;
a wire coil that surrounds the magnetic bar; and
a permanent magnet supported by the brush holder in the vicinity of the bar, the magnet exerting an attractive force on the second end of the bar when electric current is passed through the coil in a first direction and exerting a repulsive force on the second end of the bar when electric current is passed through the coil in a second direction.

11. A cleaning apparatus as claimed in claim 9 wherein the vibrator comprises a piezoelectric element.

12. A teeth cleaning apparatus comprising:
a brush comprising an elongated brush handle and a teeth cleaning member carried by the handle and having an axis extending substantially perpendicular to the brush handle;
a brush holder for supporting the brush handle to permit the movement of the brush handle in a prescribed direction such that the teeth cleaning member is moved substantially parallel to its axis;
a vibrator for vibrating the brush handle in the prescribed direction in response to an electrical drive signal; and
a signal generator for generating the drive signal, the signal generator comprising a musical reproduction device.

13. A teeth cleaning apparatus comprising:
a brush comprising an elongated brush handle and a teeth cleaning member carried by the handle and having an axis extending substantially perpendicular to the brush handle;
a brush holder for supporting the brush handle to permit the movement of the brush handle in a prescribed direction such that the teeth cleaning member is moved substantially parallel to its axis;
a vibrator for vibrating the brush handle in the prescribed direction in response to an electrical drive signal; and
a signal generator for generating the drive signal, the drive signal comprising a first frequency modulated by a second frequency lower than the first frequency.

14. A teeth cleaning apparatus comprising:
a brush comprising an brush handle and a teeth cleaning member carried by the handle and having an axis extending substantially perpendicular to the brush handle;
a brush holder for supporting the brush handle to permit the movement of the brush handle in a prescribed direction such that the teeth cleaning member is moved substantially parallel to its axis;
a vibrator for vibrating the brush handle in the prescribed direction in response to an electrical drive signal;
a signal generator for generating the drive signal;
a transmitter connected to the signal generator for transmitting the drive signal; and
a receiver mounted on the brush holder and connected to the vibrator for receiving the transmitted drive signal and providing it to the vibrator.

15. A teeth cleaning apparatus comprising:
a brush comprising an elongated brush handle and a teeth cleaning member carried by the handle and having an axis extending substantially perpendicular to the brush handle;
a brush holder for supporting the brush handle to permit the movement of the brush handle in a prescribed direction such that the teeth cleaning member is moved substantially parallel to its axis;
a vibrator for vibrating the brush handle in the prescribed direction in response to an electrical drive signal; and
a signal generator for generating the drive signal, the signal generator comprising a semiconductor memory having data corresponding to music stored therein.

16. A teeth cleaning apparatus as claimed in claim 15 wherein the semiconductor memory is supported by the brush holder, further comprising an amplifier supported by the brush holder and electrically connected to the vibrator.

17. A teeth cleaning apparatus comprising:
a brush comprising an elongated brush handle and a teeth cleaning member carried by the handle and having an axis extending substantially perpendicular to the brush handle;
a brush holder for supporting the brush handle to permit the movement of the brush handle in a prescribed direction such that the teeth cleaning member is moved substantially parallel to its axis;

a vibrator for vibrating the brush handle in the prescribed direction, the vibrator comprising a piezoelectric element having electrodes and being mechanically coupled to the brush handle;

means for generating electricity at one frequency from mechanical deformation of the element produced by a user while brushing and using the generated electricity to vibrate the element at a different frequency; and means for storage of the generated electricity.

18. A teeth cleaning apparatus comprising:

a brush comprising a brush handle and a teeth cleaning member secured to the handle, the teeth cleaning member having an axis;

a brush holder for pivotally supporting the brush handle to permit the movement of the brush handle in a prescribed direction such that the teeth cleaning member is moved for cleaning teeth;

an electrically operated transducer element supported by the brush holder in engagement with a portion of the brush handle; and means for generating and transmitting electrical signals including audio frequency signals in a range of about 100–17,000 Hz to said element and for causing said element to vibrate in response to the audio frequency signals and transmit such vibration to a user's auditory system via the brush when the brush is used for brushing teeth.

19. A teeth cleaning apparatus according to claim 18 wherein the electrical signals produced by said generating and transmitting means include signals having a substantially fixed frequency between 1,000–17,000 Hz to vibrate the cleaning member for cleaning teeth and wherein the audio frequency signals are of mixed frequency and amplitude representing music or other pleasant sounds.

20. A teeth cleaning apparatus according claim 18 wherein the signals are solely audio frequency signals of mixed frequency and amplitude representing music or other pleasant sounds.

* * * * *